(12) United States Patent
Snyder et al.

(10) Patent No.: US 11,413,085 B2
(45) Date of Patent: Aug. 16, 2022

(54) CRYOPROBE

(71) Applicant: Medtronic Holding Company Sàrl, Tolochenaz (CH)

(72) Inventors: Lloyd M. Snyder, Collierville, TN (US); Brian D. Koch, Memphis, TN (US); Aneta Samaranska, Blaine, MN (US); Jeff R. Justis, Germantown, TN (US)

(73) Assignee: MEDTRONIC HOLDING COMPANY SÀRL, Tolochenaz (CH)

( * ) Notice: Subject to any disclaimer, the term of this patent is extended or adjusted under 35 U.S.C. 154(b) by 1295 days.

(21) Appl. No.: 15/499,156

(22) Filed: Apr. 27, 2017

(65) Prior Publication Data

US 2018/0310976 A1    Nov. 1, 2018

(51) Int. Cl.
*A61B 18/02*    (2006.01)
*A61B 17/00*    (2006.01)
*A61B 18/00*    (2006.01)

(52) U.S. Cl.
CPC .... *A61B 18/02* (2013.01); *A61B 2017/00477* (2013.01); *A61B 2018/00172* (2013.01);
(Continued)

(58) Field of Classification Search
CPC ........... A61B 2017/00477; A61B 2018/00172; A61B 2018/00577; A61B 2018/0212; A61B 2018/0281; A61B 18/02
(Continued)

(56) References Cited

U.S. PATENT DOCUMENTS

| 5,452,582 A | 9/1995 | Longsworth |
| 5,520,682 A | 5/1996 | Bansi et al. |

(Continued)

FOREIGN PATENT DOCUMENTS

| CN | 1164382 A | 11/1997 |
| CN | 1812748 | 8/2006 |

(Continued)

OTHER PUBLICATIONS

Ahmed et al., Image-Guided Thermal Tumor Ablation, Radiology Key, Chapter 140, https://radiologykey.com/image-guided-thermal-tumor-ablation-basic-science-and-combination-therapies, 9 pages.
(Continued)

*Primary Examiner* — Linda C Dvorak
*Assistant Examiner* — Ryan T Clark

(57) ABSTRACT

A cryoprobe is used during surgery in a human body to remove unwanted tissue. The cryoprobe includes a first gas supply line and a second gas supply line for delivering a supply of cryogenic gas from at least adjacent a proximal end to at least adjacent a distal end of the cryoprobe. The cryoprobe further includes a first gas return line and a second gas return line for returning the supply of cryogenic gas from at least adjacent the distal end to at least adjacent the proximal end of the cryoprobe. At least a portion of the first gas supply line is received in the first gas return line. A transition portion having at least one internal cavity and an aperture from the at least one internal cavity to an exterior portion of the transition portion is also included in the cryoprobe. The transition portion is provided to facilitate at least the transfer of the cryogenic gas from the second gas return line to the first gas return line, so that the cryogenic gas can flow adjacent the first gas supply line on its way to the proximal end of the cryoprobe.

23 Claims, 11 Drawing Sheets

(52) U.S. Cl.
CPC ............ *A61B 2018/00577* (2013.01); *A61B 2018/0212* (2013.01); *A61B 2018/0281* (2013.01)

(58) Field of Classification Search
USPC ............... 606/20, 21, 22, 23, 24, 25, 26, 27
See application file for complete search history.

(56) References Cited

U.S. PATENT DOCUMENTS

| | | | |
|---|---|---|---|
| 5,674,218 | A | 10/1997 | Rubinsky et al. |
| 5,720,743 | A | 2/1998 | Bischof et al. |
| 6,039,730 | A | 3/2000 | Rabin et al. |
| 6,270,494 | B1 | 8/2001 | Kovalcheck et al. |
| 6,306,129 | B1 | 10/2001 | Little et al. |
| 6,379,348 | B1 | 4/2002 | Onik |
| 6,503,246 | B1 | 1/2003 | Har-Shai et al. |
| 7,238,184 | B2 | 7/2007 | Megerman et al. |
| 7,479,139 | B2 | 1/2009 | Cytron et al. |
| 7,485,117 | B2 * | 2/2009 | Damasco ............... A61B 18/02 606/20 |
| 9,033,966 | B2 | 5/2015 | McKay |
| 9,345,528 | B2 | 5/2016 | Laske et al. |
| 2001/0037812 | A1 | 11/2001 | Dobak et al. |
| 2002/0022832 | A1 | 2/2002 | Mikus et al. |
| 2002/0049436 | A1 | 4/2002 | Zvuloni et al. |
| 2002/0087152 | A1 | 7/2002 | Mikus et al. |
| 2003/0181896 | A1 | 9/2003 | Zvuloni et al. |
| 2004/0267248 | A1 | 12/2004 | Duong et al. |
| 2005/0090779 | A1 | 4/2005 | Osypka |
| 2006/0079867 | A1 * | 4/2006 | Berzak ................. A61B 18/02 606/21 |
| 2006/0264920 | A1 | 11/2006 | Duong |
| 2007/0191732 | A1 | 8/2007 | Voegele |
| 2008/0027422 | A1 | 1/2008 | Vancelette et al. |
| 2008/0051776 | A1 | 2/2008 | Bliweis et al. |
| 2008/0114346 | A1 | 5/2008 | Levin et al. |
| 2008/0119836 | A1 | 5/2008 | Littrup et al. |
| 2008/0119838 | A1 | 5/2008 | Vancelette et al. |
| 2008/0147055 | A1 | 6/2008 | Duong et al. |
| 2008/0154258 | A1 | 6/2008 | Chang et al. |
| 2009/0299357 | A1 | 12/2009 | Zhou |
| 2011/0015624 | A1 | 1/2011 | Toubia et al. |
| 2011/0178514 | A1 | 7/2011 | Levin et al. |
| 2011/0264084 | A1 | 10/2011 | Reid |
| 2012/0089211 | A1 | 4/2012 | Curtis et al. |
| 2012/0265186 | A1 | 10/2012 | Burger et al. |
| 2014/0275767 | A1 | 9/2014 | Baust |
| 2014/0303616 | A1 * | 10/2014 | Shin ..................... A61N 1/06 606/40 |
| 2015/0094700 | A1 | 4/2015 | Iwata |

FOREIGN PATENT DOCUMENTS

| | | |
|---|---|---|
| CN | 101396299 A | 4/2009 |
| CN | 104605925 | 5/2015 |
| CN | 104758049 | 7/2015 |
| CN | 206044717 | 3/2017 |
| EP | 108112 | 9/1988 |
| EP | 0955012 | 11/1999 |
| GB | 2283678 | 5/1995 |
| RU | 154699 U1 | 9/2015 |
| WO | WO9965410 | 12/1999 |
| WO | WO0113782 | 3/2001 |
| WO | WO2005/000106 | 1/2005 |

OTHER PUBLICATIONS

Kecheng Xu, Apparatus and Principle of Cryosurgery, FUDA Cancer Hospital—Guangzhou//cancer treatment china, http://www.fudahospital.com/id_asp_new/show_crosurgery_book.asp?page=crosurgery_1_2, Jun. 9, 2017, 4 pages.

Maria, et al., Percutaneous Cryoablation for Renal Cell Carcinoma, Journal of Kidney Cancer and VHL, 2015; 2(3): 105-113. Doi: http://dx.doi.org/10.15586/jkcvhl.2015.34, Codon Publications, Brisbane, Australia, ISSN 2203-5826, 7 pages.

European Search Report dated Aug. 21, 2018 in European Application No. 18163082.3.

European Search Report dated Jul. 27, 2021 in European Application No. 18162809.0.

Office Action dated Dec. 3, 2021 in Chinese Application No. 201810342105.3.

* cited by examiner

CRYOPROBE

BACKGROUND OF THE INVENTION

Field of the Invention

The present invention relates to a cryoprobe employing the Joule-Thom son effect to generate cryogenic temperatures for use during surgery on a patient. More particularly, the present invention relates to a cryoprobe for use in ablating unwanted tissue of a patient during surgery by freezing the unwanted tissue using cryogenic temperatures generated thereby. The present invention relates to a cryoprobe for use during surgery that is configured to facilitate precooling of cryogenic supply gas using cryogenic return gas after the cryogenic return gas has been subjected to the Joule-Thomson effect.

Description of the Prior Art

Typically, cryoprobes used for ablation of unwanted tissue during surgery use the Joule-Thomson effect to generate cryogenic temperatures. In these cryoprobes, cryogenic supply gas is provided to portions of the cryoprobes that cause expansion of the cryogenic gas. Expansion of the cryogenic supply gas further cools the gas via the Joule-Thomson effect. However, there is a need for a cryoprobe with increased efficiency. To that end, there is a need for a cryoprobe configured to afford use of cooling gas after effectuation of the Joule-Thomson effect. Such a cryoprobe can use cryogenic return gas to precool cryogenic supply gas during flow of the cryogenic gas through the cryoprobe.

SUMMARY OF THE INVENTION

The present invention in one preferred embodiment contemplates a cryoprobe for use during surgery in a human body to remove unwanted tissue, the cryoprobe having a proximal end and a distal end opposite from one another; a first gas supply line and a second gas supply line for delivering a supply of cryogenic gas from at least adjacent the proximal end to at least adjacent the distal end, the first gas supply line being connected to a supply of cryogenic gas; a first gas return line and a second gas return line for returning the supply of cryogenic gas from at least adjacent the distal end to at least adjacent the proximal end; a first portion of the first gas supply line extending through a first portion of the first gas return line; at least one turbulence inducer provided in the first gas return line between the first gas supply line and the first gas return line; a transition portion having at least one internal cavity and an aperture from the at least one internal cavity to an exterior portion of the transition portion, an end of a second portion of the first gas return line being attached to the transition portion, an end of a second portion of the first gas supply line being received in the internal cavity of the transition portion, an end of a first portion of the second gas return line being received in the transition portion, and an end of a first portion of the second gas supply line being received in the internal cavity of the transition portion, the ends of the second portion of the first gas supply line and the first portion of the second gas supply line being coupled to one another within the internal cavity of the transition portion; and a probe portion including a shaft portion, the shaft portion including a first end, a second end, and an interior cavity extending from adjacent the first end to adjacent the second end, the shaft portion including an opening into the interior cavity at the first end, and a tip at second end, a second portion of the second gas return line extending into the interior cavity of the shaft portion, a second portion of the second gas supply line extending through the second portion of the second gas return line, the second portion of the second gas return line terminating at an end within the interior cavity and the second portion of the second gas supply line terminating at an end within the interior cavity, the end of the second portion of the second gas supply line being closer to the tip than the end of the second portion of the second gas return line; where the cryogenic gas is supplied to the interior cavity of the shaft portion via travel through at least the first gas supply line and the second gas supply line, and the cryogenic gas is returned to at least adjacent the proximal end via travel through at least the second gas return line, the transition portion, and the first gas return line, the cryogenic gas being returned first flowing adjacent the second gas supply line in the second gas return line, the cryogenic gas being returned second flowing into the internal cavity of the transition portion from the second gas return line, the cryogenic gas being returned third flowing through the aperture in the transition portion from the internal cavity of the transition portion to a gap between the first gas return line and the transition portion, the cryogenic gas being returned fourth flowing adjacent the first gas supply line in the first gas return line from the gap between the first gas return line and the transition portion, the at least one turbulence inducer creating turbulence in the cryogenic gas being returned flowing through the first gas return line.

The present invention in another preferred embodiment contemplates a cryoprobe for use during surgery in a human body to remove unwanted tissue, the cryoprobe having a proximal end and a distal end opposite from one another; a first gas supply line and a second gas supply line for delivering a supply of cryogenic gas from at least adjacent the proximal end to at least adjacent the distal end, the first gas supply line being connected to a supply of cryogenic gas; a first gas return line and a second gas return line for returning the supply of cryogenic gas from at least adjacent the distal end to at least adjacent the proximal end; a first portion of the first gas supply line extending through a first portion of the first gas return line; a head portion including at least one interior cavity extending therethrough, the head portion including a transition portion being at least partially received in the at least one interior cavity, the transition portion having at least one internal cavity and an aperture from the at least one internal cavity to an exterior portion of the transition portion, a second portion of the first gas return line and a second portion of the first gas supply line extending into the head portion, an end of the second portion of the first gas return line being attached to the transition portion such that a gap is formed between the exterior portion of the transition portion and the first return gas line, an end of the second portion of the first gas supply line being received in the internal cavity of the transition portion, an end of a first portion of the second gas return line being received in the transition portion, and an end of a first portion of the second gas supply line being received in the internal cavity of the transition portion, the ends of the second portion of the first gas supply line and the first portion of the second gas supply line being coupled to one another within the internal cavity of the transition portion; and a probe portion attached to the head portion, the probe portion including a coupler portion and a shaft portion, the coupler portion being attached to the head portion, and the shaft portion extending outwardly from the coupler portion, the shaft portion including a first end, a second end, and an interior cavity extending from adjacent the first end to adjacent the second end, the shaft portion including an opening into the interior cavity at the first end, and a tip at the second end, a second portion of the second gas return line extending from the head portion through the coupler portion and into the interior cavity of the shaft portion, and a second portion of the second gas supply line extending through the second portion of the second gas return line, the second portion of the second gas return line terminating at an end within the interior cavity and the second portion of the second gas supply line terminating at an end within the interior cavity, the end of the second portion of the second gas supply line being closer to the tip than the end of the second portion of the second gas return line; where the cryogenic gas is supplied to the interior cavity of the shaft portion via travel through at least the first gas supply line and the second gas supply line, and the cryogenic gas is returned to at least adjacent the proximal end via travel through at least the second gas return line, the transition portion, and the first gas return line, the cryogenic gas being returned first flowing adjacent the second gas supply line in the second gas return line, the cryogenic gas being returned second flowing into the internal cavity of the transition portion from the second gas return line, the cryogenic gas being returned third flowing through the aperture in the transition portion from the internal cavity of the transition portion to the gap between the first gas return line and the transition portion, the cryogenic gas being returned fourth flowing adjacent the first gas supply line in the first gas return line from the gap between the first gas return line and the transition portion.

The present invention in yet another preferred embodiment contemplates a cryoprobe for use during surgery in a human body to remove unwanted tissue, the cryoprobe having a proximal end and a distal end opposite from one another; a first gas supply line and a second gas supply for delivering a supply of cryogenic gas from at least adjacent the proximal end to at least adjacent the distal end, the first gas supply line being connected to a supply of cryogenic gas; a first gas return line and a second gas return line for returning the supply of cryogenic gas from at least adjacent the distal end to at least adjacent the proximal end; a first portion of the first gas supply line extending through a first portion of the first gas return line; a head portion including at least one interior cavity extending therethrough, the head portion including a transition portion being at least partially received in the at least one interior cavity, the transition portion having at least one internal cavity and an aperture from the at least one internal cavity to an exterior portion of the transition portion, a second portion of the first gas return line and a second portion of the first gas supply line extending into the head portion, an end of the second portion of the first gas return line being attached to the transition portion such that a gap is formed between the exterior portion of the transition portion and the first return gas line, an end of the second portion of the first gas supply line being received in the internal cavity of the transition portion, an end of a first portion of the second gas return line being received in the transition portion, and an end of a first portion of the second gas supply line being received in the internal cavity of the transition portion, the ends of the second portion of the first gas supply line and the first portion of the second gas supply line being coupled to one another within the internal cavity of the transition portion; and a probe portion attached to the head portion, the probe portion including a coupler portion and a shaft portion, the coupler portion being attached to the head portion, and the shaft portion extending outwardly from the coupler portion, the shaft portion including a first end, a second end, and an interior cavity extending from adjacent the first end to adjacent the second end, the shaft portion including an opening into the interior cavity at the first end, and a tip at the second end, a second portion of the second gas return line extending from the head portion through the coupler portion and into the interior cavity of the shaft portion, and a second portion of the second gas supply line extending through the second portion of the second gas return line, the second portion of the second gas return line terminating at an end within the interior cavity and the second portion of the second gas supply line terminating at an end within the interior cavity, the end of the second portion of the second gas supply line being closer to the tip than the end of the second portion of the second gas return line; where the cryogenic gas is supplied to the interior cavity of the shaft portion via travel through at least the first gas supply line and the second gas supply line, and the cryogenic gas is returned to at least adjacent the proximal end via travel through at least the second gas return line, the transition portion, and the first gas return line, the cryogenic gas being returned first flowing adjacent the second gas supply line in the second gas return line, the cryogenic gas being returned second flowing into the internal cavity of the transition portion from the second gas return line, the cryogenic gas being returned third flowing through the aperture in the transition portion from the internal cavity of the transition portion to the gap between the first gas return line and the transition portion, the cryogenic gas being returned fourth flowing adjacent the first gas supply line in the first gas return line from the gap between the first gas return line and the transition portion.

These and other objects of the present invention will be apparent from review of the following specification and the accompanying drawings.

DETAILED DESCRIPTION OF THE PREFERRED EMBODIMENT

In accordance with one preferred embodiment of the present invention, and, as depicted in FIGS. 1-11, a cryoprobe generally indicated by the numeral 10 is provided for use during surgery to facilitate ablation of unwanted tissue inside the body of a patient.

Figure 1:
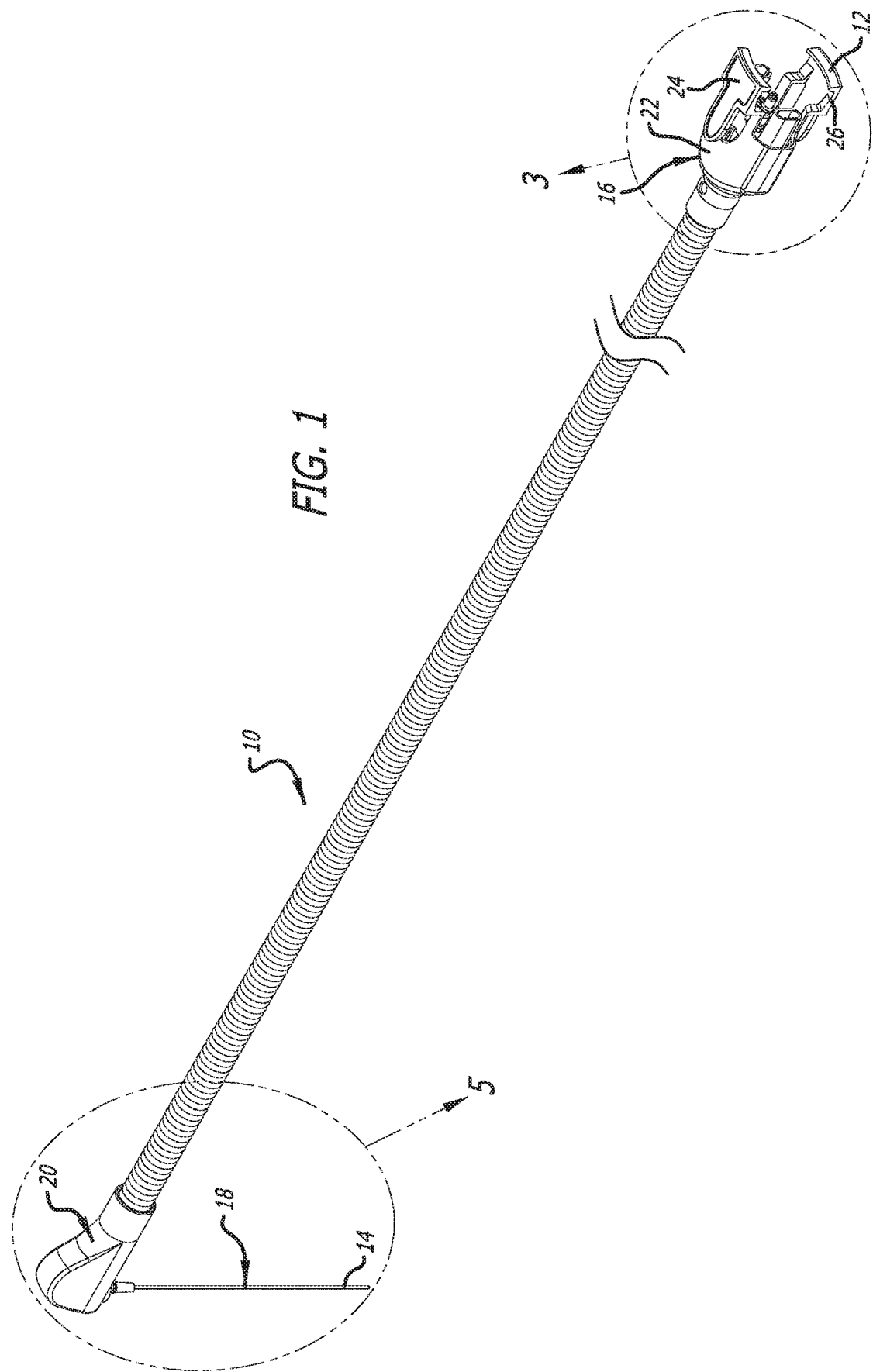
FIG. 1 is a perspective view a cryoprobe according to an embodiment of the present invention.
Figure 2:
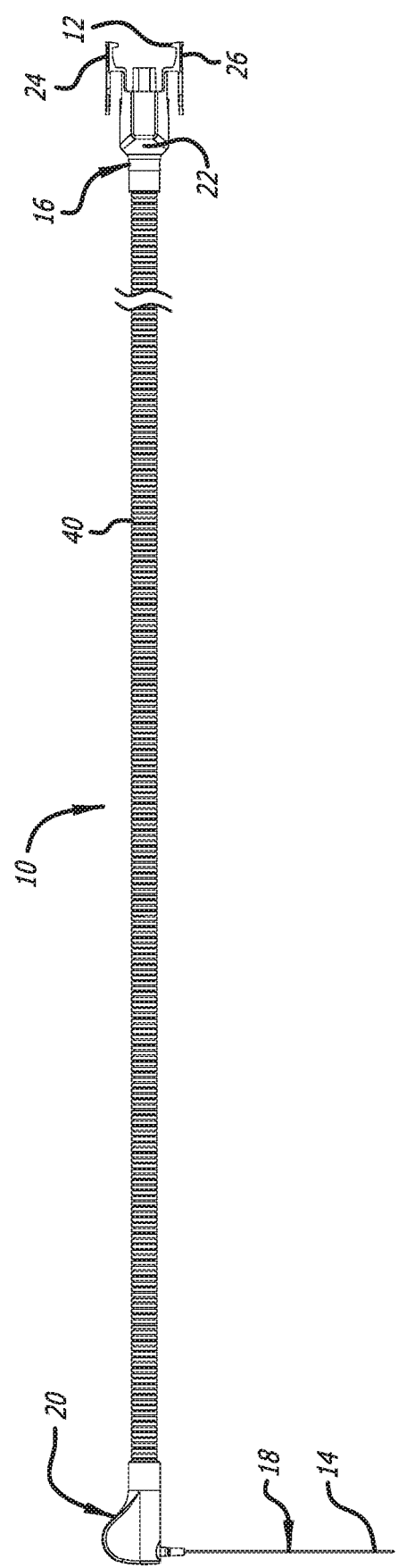
FIG. 2 is a side elevational view of the cryoprobe of FIG. 1.

The cryoprobe 10, as depicted in FIGS. 1 and 2, includes a proximal end 12 and a distal end 14 opposite from one another. As discussed below, the cryoprobe 10 includes an end portion 16 provided at the proximal end 12, a probe portion 18 provided at the distal end 14, and a head portion 20 positioned between the proximal end 12 and the distal end 14. The various components of the cryoprobe 10 can be made of metallic and polymeric materials. However, it is noted that polymeric materials can be used where insulative properties are desirous, and the metallic materials can be used where heat transfer properties are desirous. Furthermore, the tubes and the supply/return lines discussed below can be cylindrical to facilitate ease of construction, but the tubes and the supply/return lines can have other shapes and configurations.

To facilitate ablation of unwanted tissue, a portion of the cryoprobe 10 is inserted into the body of the patient. The cryoprobe 10 is capable of generating external cryogenic temperatures (e.g., ranging from −80 to −120° C.) on an exterior portion of the probe portion 18 adjacent the distal end 14, and thus, the portion of the probe portion 18 serves as a heat exchanger to facilitate ablation of the unwanted tissue via freezing thereof using the cryogenic temperatures. In doing so, the cryoprobe 10 is capable of generating internal cryogenic temperatures (e.g., ranging from −100° C. to −150° C.). For example, a surgeon can use the cryoprobe 10 to surgically ablate cancerous tumors via the freezing thereof. As discussed below, the cryoprobe 10 employs the Joule-Thomson effect to generate the cryogenic temperatures in the probe portion 18. To that end, the cryoprobe 10 uses a supply of cryogenic gas from a cryogenic gas supply (not shown) that can be turned on and off as needed. The flow of cryogenic gas through the cryoprobe 10 is indicated by various arrows in FIGS. 4 and 7-11. Supply gas travels from the cryogenic gas supply through the cryoprobe from the proximal end 12 to the distal end 14, and return gas travels from the distal end 14 to the proximal end 12.

Figure 3:
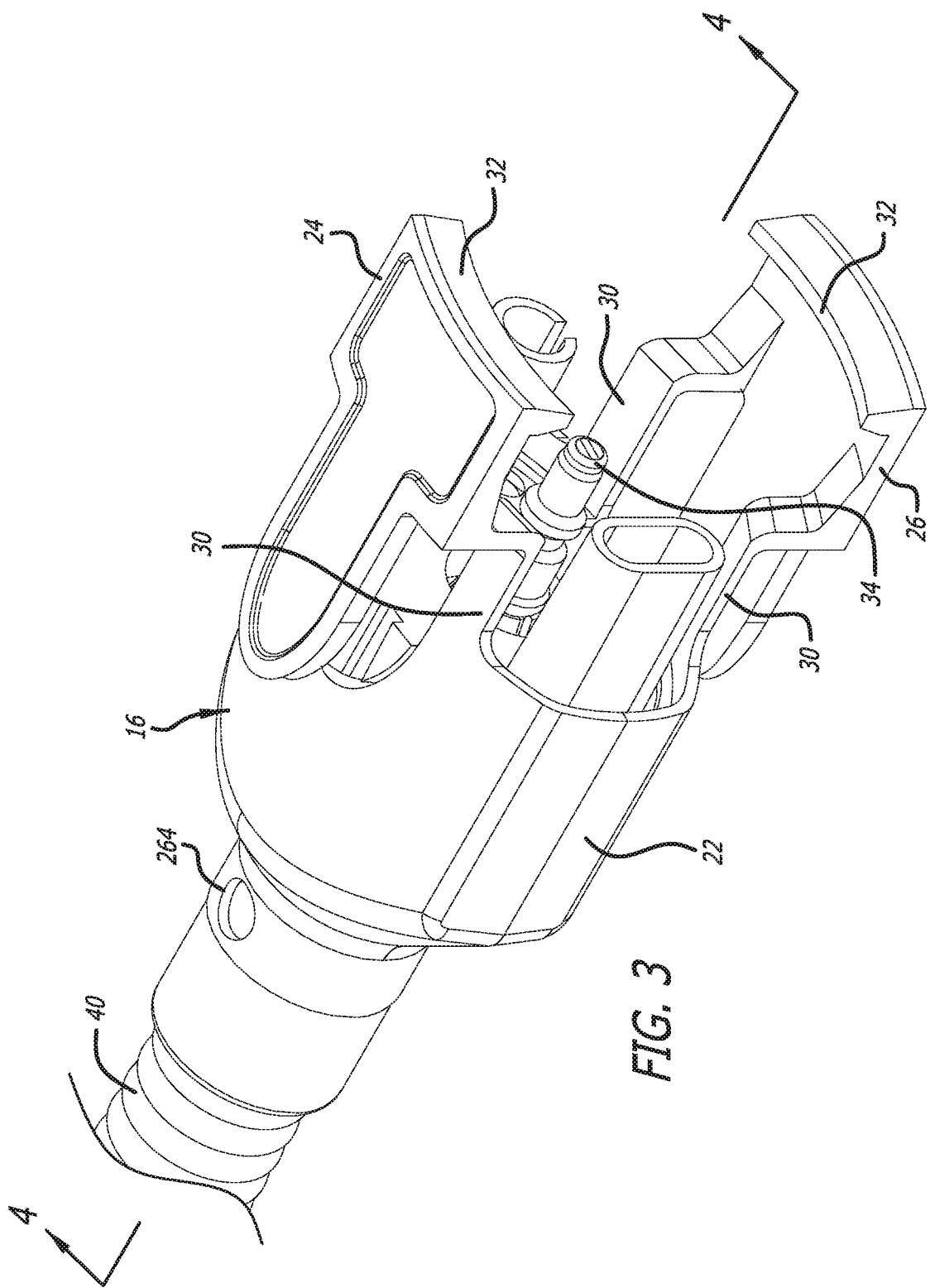
FIG. 3 is an enlarged view of an end portion of the cryoprobe of FIG. 1.
Figure 4:
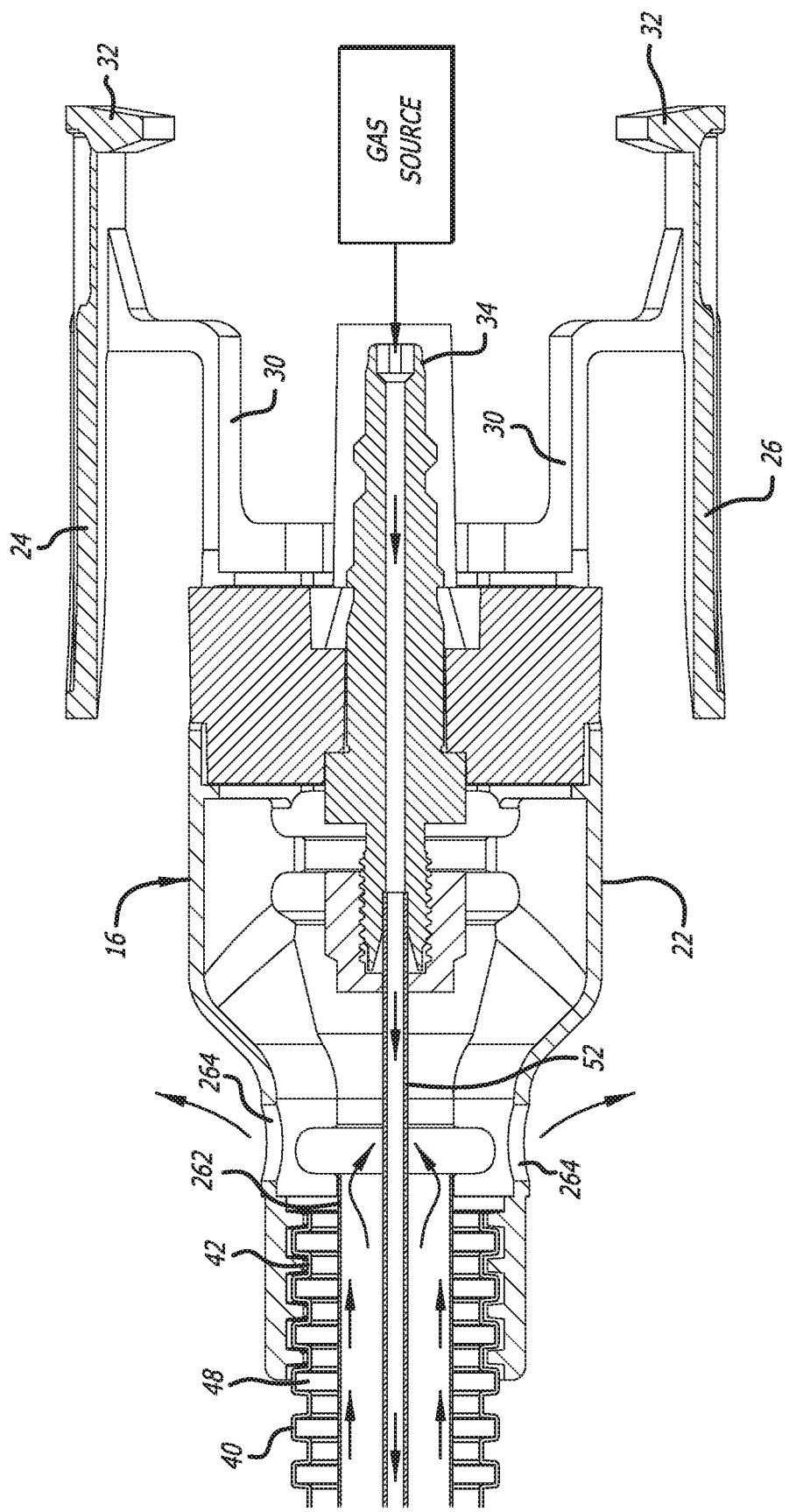
FIG. 4 is a cross-sectional view of the end portion of the cryoprobe taken along Line 4-4 of FIG. 3.

The cryoprobe 10 includes an end portion 16 provided at the proximal end 12 for facilitating interconnection with the cryogenic gas supply. As depicted in FIGS. 3 and 4, the end portion 16 includes a body portion 22, and a first arm portion 24 and a second arm portion 26 attached to the body portion 22. The first and second arm portions 24 and 26 are each attached to the body portion 22 via connecting portions 30, and each of the first and second arm portions 24 and 26 include latching portions 32. The connecting portions 30 allow the first and second arm portions 24 and 26 to pivot with respect to the body portion 22, and such pivotal movement allows the latching portions 32 to move inwardly and outwardly with respect to one another. The latching portions 32 can be used to engage complementary structures provided on the cryogenic gas supply, and such engagement can serve to connect the cryoprobe 10 to the cryogenic gas supply.

In addition to facilitating attachment to the cryogenic gas supply, the end portion 16 also includes an inlet connector 34 for engaging a complementary structure (not shown) on the cryogenic gas supply. As depicted in FIG. 4, the inlet connector 34 extends through the end portion 16. The inlet connector 34 facilitates connection of the cryoprobe 10 to a supply of gas provided by the cryogenic gas supply. The supply gas provided by the cryogenic gas supply can include Argon, Krypton, Xenon, $CO_2$, $N_2O$, and $N_2$, for example. The supply gas provided by the cryogenic gas supply is provided at a high pressure (e.g., ranging from 3000 to 3400 psi) to facilitate use of the Joule-Thomson effect by the cryoprobe 10.

Figure 5:
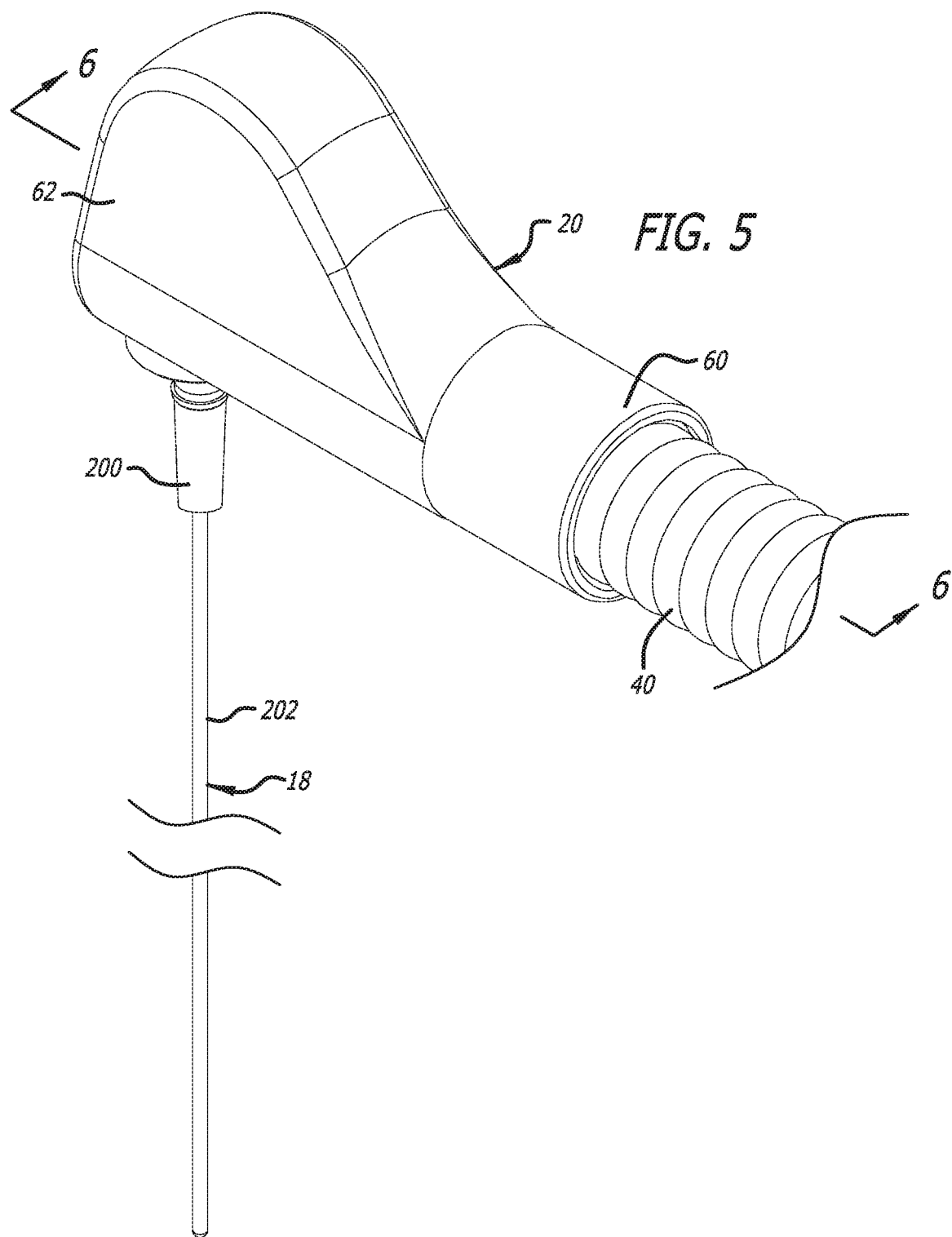
FIG. 5 is an enlarged view of a head portion of the cryoprobe of FIG. 1.
Figure 6:
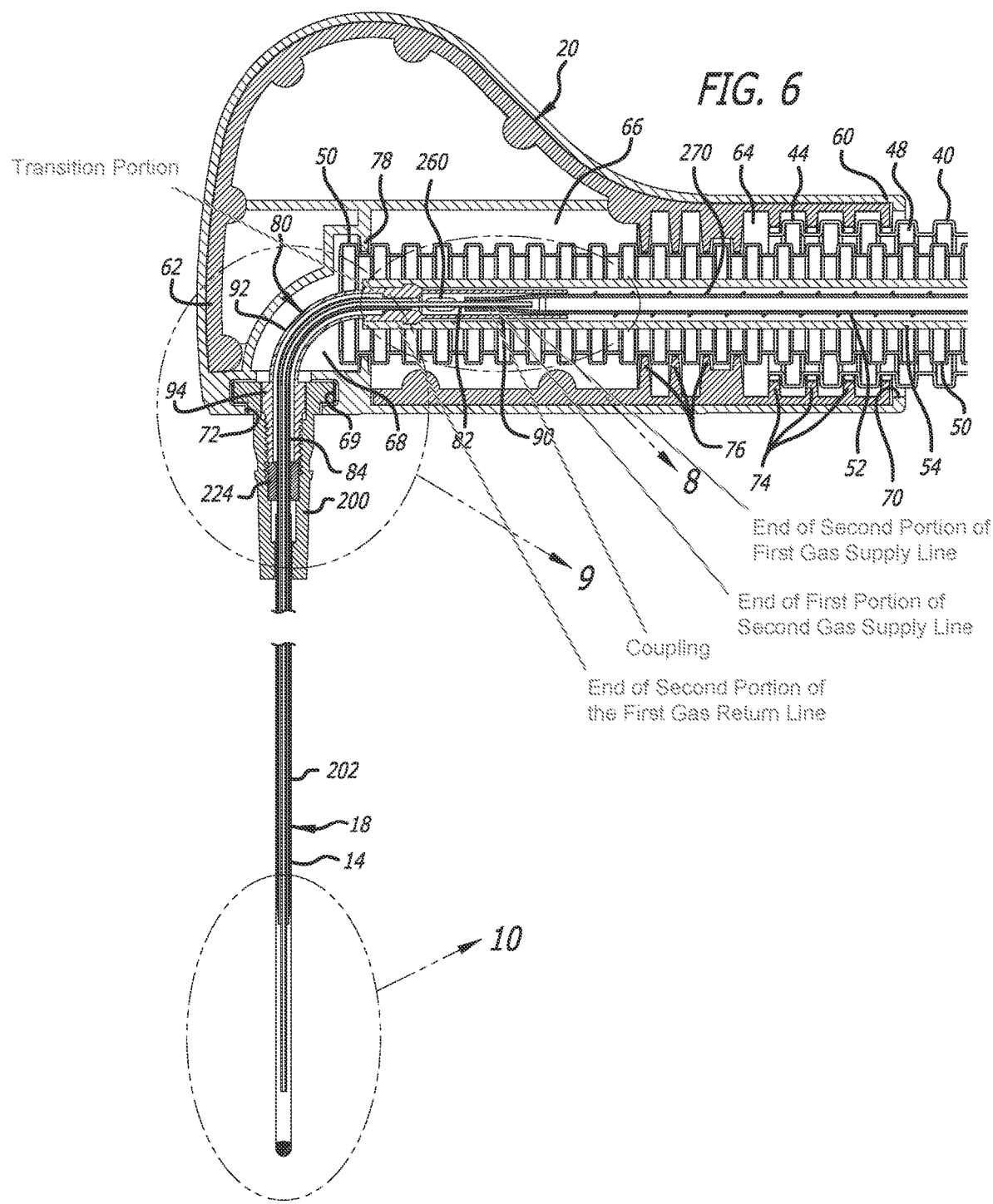
FIG. 6 is a cross-sectional view of the head portion of the cryoprobe taken along Line 6-6 of FIG. 5.

As depicted in FIGS. 3-6 and 11, the cryoprobe 10 further includes an exterior tube 40 having a first end 42 and a second end 44. The first end 42 of the exterior tube 40 is attached (FIGS. 3 and 4) to the end portion 16, and the second end 44 of the exterior tube 40 is attached to the head portion 20 (FIGS. 5 and 6). The exterior tube 40 includes an interior 48, and the interior 48 contains internal structures that facilitate transfer of the supply gas from the end portion 16 to the head portion 20, and contains internal structures that facilitate transfer of return gas from the head portion 20 to the end portion 16. The exterior tube 40 affords protection of the internal structures, and the exterior tube 40 is flexible. The exterior tube 40 can be corrugated or convoluted to afford such flexibility. The flexibility of the exterior tube 40 affords manipulation thereof during surgery, and thus, the exterior tube 40 affords positioning and repositioning of the head portion 20.

The interior 48 of the exterior tube 40, as depicted in FIG. 6, includes an interior tube 50, a first gas supply line 52, and a first gas return line 54 extending therethrough. Like the exterior tube 40, the interior tube 50, the first gas supply line 52, and the first gas return line 54 can be flexible. The interior tube 50 can be corrugated or convoluted to afford such flexibility, and the first gas supply line 52 and the first gas return line 54 can be made of flexible materials. The first gas supply line 52 is interconnected with the inlet connector 34 (FIG. 4), and is used in facilitating passage of the supply gas to adjacent the distal end 14. Specifically, the first gas supply line 52 is configured to transfer the supply gas from the cryogenic gas supply to the head portion 20. Furthermore, the first gas return line 54 is used in facilitating passage of the return gas to adjacent the proximal end 12. The first gas supply line 52 is received inside the first gas return line 54, the first gas return line 54 is received inside the interior tube 50, and the interior tube 50 is received inside the exterior tube 40. Like the exterior tube 40, the interior tube 50 is flexible, and can be corrugated or convoluted and made of semi-rigid polymeric and/or polymeric materials to afford protection of the internal structures, where the corrugation or convolution thereof can afford such flexibility. The flexibility of the exterior tube 40, the interior tube 50, the first gas return line 54, and the first gas supply line 52 affords manipulation thereof during surgery to afford positioning and repositioning of the head portion 20.

The head portion 20, as depicted in FIGS. 5 and 6, includes a first end portion 60 and a second end portion 62. As depicted in FIG. 6, the head portion 20 is hollow, and includes at least a first internal cavity 64, a second internal cavity 66, a third internal cavity 68, and a fourth internal cavity 69. The first end portion 60 includes a first aperture 70 communicating with the first internal cavity 64 and sized to receive the exterior tube 40 (and portions of the interior tube 50, the first gas supply line 52, and the first gas return line 54) therethrough. The second end portion 62 includes a second aperture 72. Furthermore, the first internal cavity 64 includes a first set of internal ribs 74 that are sized to complement the corrugation of the exterior tube 40. To attach the exterior tube 40 to the head portion 20, a portion of the exterior tube 40 is inserted through the first aperture 70 into the first internal cavity 64, so that at least a portion of the first set of internal ribs 74 are press fit into the corrugation of the exterior tube 40. Such a press fit serves in holding the exterior tube 40 in position relative to the head portion 20.

Figure 7:
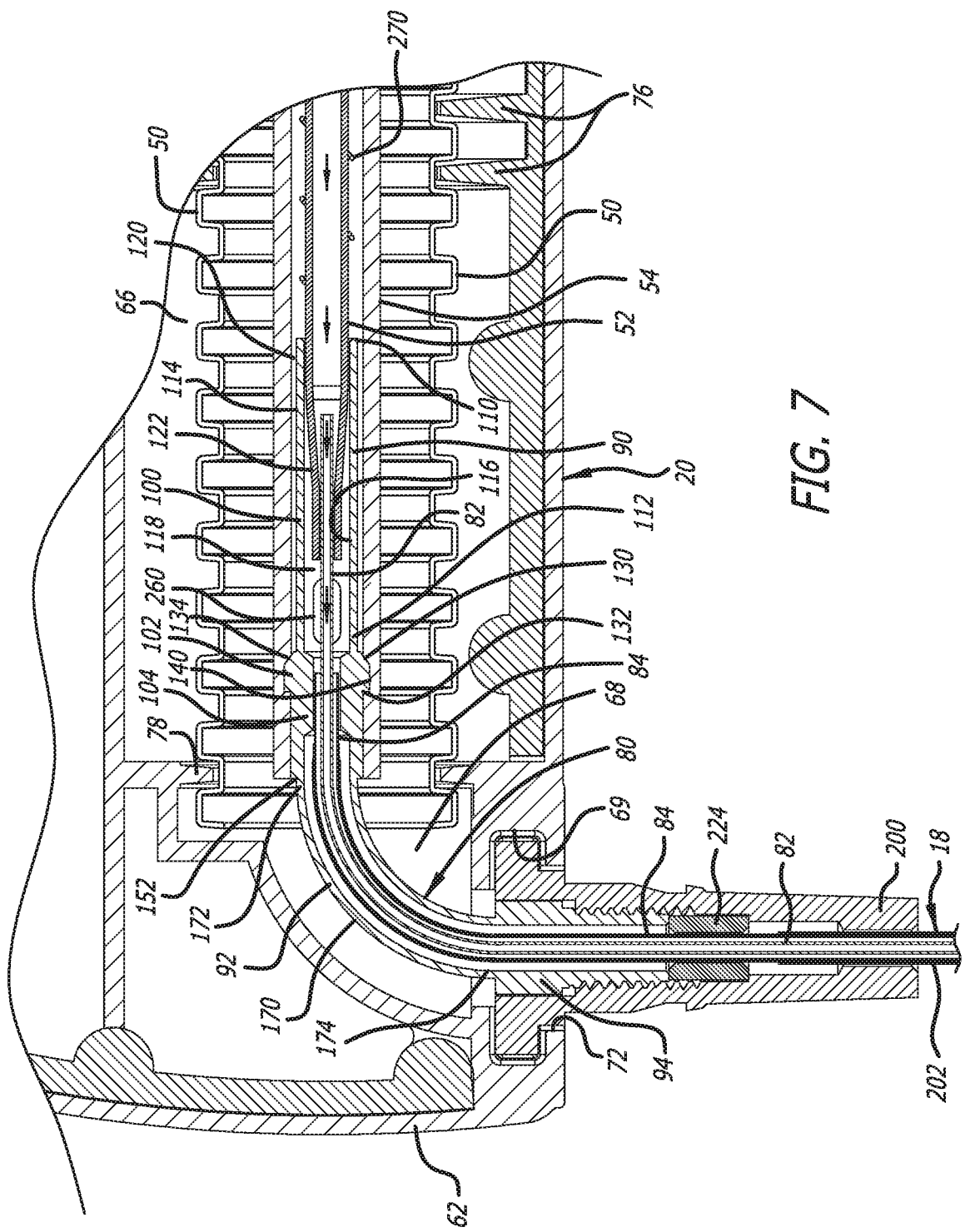
FIG. 7 is an enlarged cross-sectional view of a portion of the head portion and a portion of a probe portion of the cryoprobe of FIG. 6.

The interior tube 50 is also attached to the head portion 20 (FIGS. 6 and 7). In addition to the first set of internal ribs 74, the first internal cavity 64 also includes a second set of internal ribs 76, and a shoulder portion 78 is provided between the second internal cavity 66 and the third internal cavity 68. To attach the interior tube 50 to the head portion 20, a portion of the interior tube 50 is inserted through the first aperture 70 into the first internal cavity 64, the second internal cavity 66, and past the shoulder portion 78, so that at least a portion of the second set of internal ribs 76 and the shoulder portion 78 are press fit into the corrugation of the interior tube 50. Such a press fit serves in holding the interior tube 50 in position relative to the head portion 20.

The head portion 20 also includes a transition portion 80. The transition portion 80, as depicted in FIGS. 6-9, is provided to effectuate coupling of the first gas return line 54 to a second gas return line 84. The transition portion 80 includes a first portion 90, a second portion 92, and a third portion 94. The first portion 90 of the transition portion 80 is received on the inside of the first gas return line 54, and is formed from a first sleeve portion 100, a flange portion 102, and a second sleeve portion 104 attached to one another.

Figure 8:
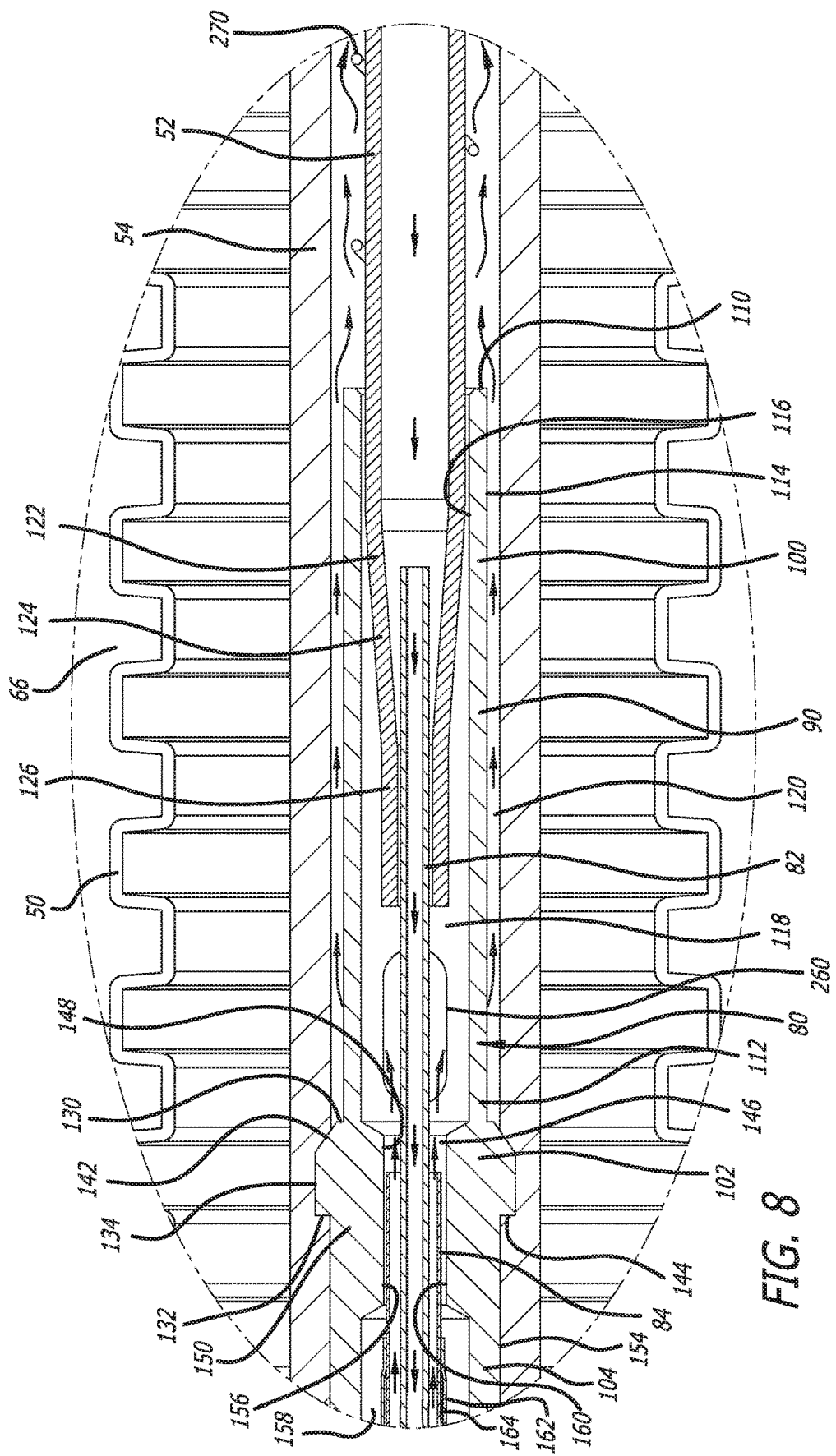
FIG. 8 is an enlarged cross-sectional view of yet another portion of the head portion of FIG. 6.

As depicted in FIGS. 7 and 8, the first sleeve portion 100 can be cylindrical, and includes a first end 110 and a second end 112. The first sleeve portion 100 also includes an exterior surface 114, an interior surface 116, and an internal cavity 118 extending between the first end 110 and the second end 112. The external dimensions of the first sleeve portion 100 (as defined by the exterior surface 114) are slightly smaller than the internal dimensions of the first gas return line 54. As such, a gap 120 is formed between the exterior surface 114 of the first sleeve portion 100 and the internal dimensions of the first gas return line 54. As discussed below, the transition portion 80 and the gap 120 (between the first gas return line 54 and the transition portion 80) are used in facilitating passage of the return gas to adjacent the proximal end 12.

The internal dimensions of the internal cavity 118 of the first sleeve portion 100 (as defined by the interior surface 116) are sized to receive the first gas supply line 52 therein. For example, the internal dimensions of the internal cavity 118 can be sized to complement the external dimensions of the first gas supply line 52. The fit between the first gas supply line 52 and the internal cavity 118 can also be fluid tight. The fluid-tight fitment between the first gas supply line 52 and the internal cavity 118 can be effectuated by crimping of the first gas supply line 52 and first sleeve portion 100 together. As such, the fit between the first gas supply line 52 and the internal cavity 118 can serve in attaching the first gas supply line 52 to the transition portion 80.

The first gas supply line 52, as depicted in FIGS. 6-8, is attached the second gas supply line 82 inside the internal cavity 118 of the first sleeve portion 100. The first gas supply line 52 includes an end portion 122 that necks down from the remainder thereof. To the end, the end portion 122 can include a frusto-conical portion 124 and a cylindrical portion 126. The frusta-conical portion 124 serves in transitioning the remainder of the first gas supply line 52 to the cylindrical portion 126. The internal dimensions of the end portion 122 are sized to receive the second gas supply line 82 therein. For example, the internal dimensions of the cylindrical portion 126 can be sized to complement the external dimensions of the second gas supply line 82. As such, the fit between the second gas supply line 82 and the cylindrical portion 126 can serve in attaching the second gas supply line 82 to the first gas supply line 52. The fit between the second gas supply line 82 and the first gas supply line 52 can be fluid tight. The fluid-tight fitment between the second gas supply line 82 and the first gas supply line 52 can be effectuated by welding or brazing. As discussed below, the second gas supply line 82 extends from the transition portion 80 and terminates in the probe portion 18. The second gas supply line 82, like the first gas supply line 52, is used in facilitating passage of the supply gas to adjacent the distal end 14.

As depicted in FIGS. 7 and 8, the flange portion 102 includes a first end 130 and a second end 132. The flange portion 102 also includes an exterior surface 134 having exterior dimensions configured to be press-fit into the first gas return line 54 and the fit between the flange portion 102 and the first gas return line 54 can be fluid tight. Furthermore, the exterior surface 134 can include a leading surface 142 (adjacent the first end 130) and a trailing surface 144 (adjacent the second end 132) for facilitating the press-fit of the flange portion 102 into the first gas return line 54. To illustrate, the leading surface 142 is angled to facilitate insertion of the flange portion 102 into the first gas return line 54, and the trailing surface 144 serves in preventing withdrawal of the flange portion 102 from the first gas return line 54.

The flange portion 102 also includes an internal cavity 146 having an interior surface 148 extending therethrough. The internal dimensions of the internal cavity 146 (as defined by the interior surface 148) are sized to receive the second gas return line 84 therein. As discussed below, the second gas return line 84 extends from the transition portion 80 and terminates in the probe portion 18, and the second gas supply line 82 extends through second gas return line 84 along its length. The second gas return line 84, like the first gas return line 54, is used in facilitating passage of the return gas to adjacent the proximal end 12.

Figure 9:
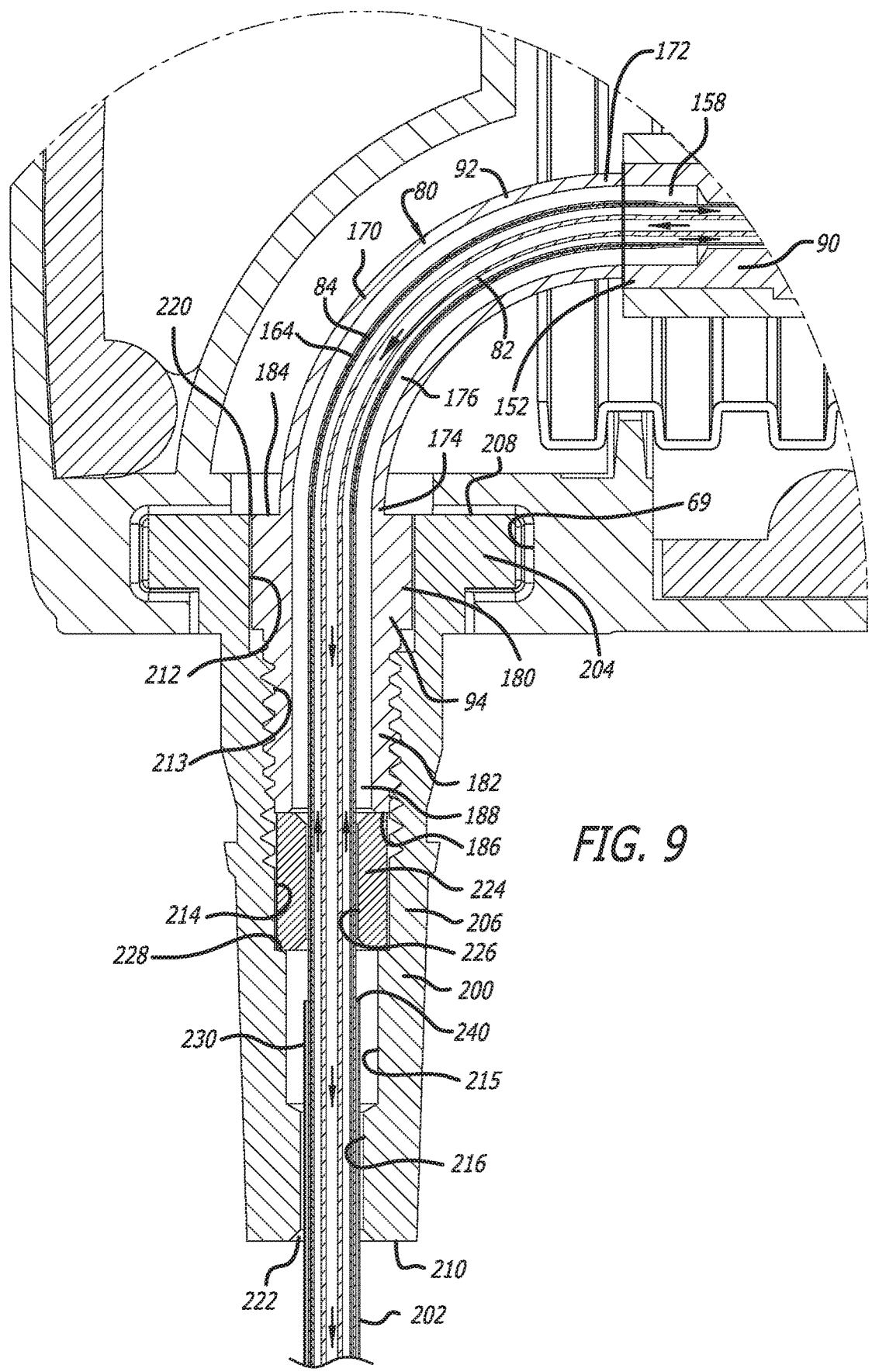
FIG. 9 is an enlarged cross-sectional view of another portion of the head portion and another portion of the probe portion of the cryoprobe of FIG. 6.

As depicted in FIGS. 7-9, the second sleeve portion 104 can be cylindrical, and includes a first end 150 and a second end 152. The second sleeve portion 104 also includes an exterior surface 154, a first internal cavity portion 156, and a second internal cavity portion 158. The exterior dimensions of the second sleeve portion 104 (as defined by the exterior surface 154) are sized to correspond to the interior dimensions of the first gas return line 54. As such, the fit between the second sleeve portion 104 and the first gas return line 54 can be fluid tight.

Together, the first internal cavity portion 156 and the second internal cavity portion 158 extend between the first end 150 and the second end 152 of the second sleeve portion 104. The first internal cavity portion 156 includes an interior surface 160. The first internal cavity portion 156 communicates with the internal cavity 146, and like the internal cavity 146, the internal dimensions of the first internal cavity portion 156 (as defined by the interior surface 160) are sized to receive the second gas return line 84 therein.

Furthermore, the second internal cavity portion 158 is sized at least to afford passage of the second gas return line 84 therethrough. The second internal cavity portion 158 is also sized to afford passage of an insulating sheath 162 that surrounds a portion of the second gas return line 84. The insulating sheath 162, as discussed below, is attached to and surrounds the portion of the second gas line 84 to create an insulative cavity 164. The insulative cavity 164, for example, can be filled with an insulative material and/or gas to insulate against the cooling effect of the cold gas traveling through the second gas return line 84. For example, the insulating sheath 162 can be formed for Insulon® from Concept Group, Inc., and the insulative cavity 164 can be a pulled vacuum. As such, the insulative cavity 164 serves in isolating the second gas return line 84 (and the second gas supply line 82 running therethrough) from various portions of the cryoprobe 10.

As discussed above, the second gas supply line 82 and the second gas return line 84 extend from the translation portion 80 and terminate in the probe portion 18. As such, the second portion 92 and the third portion 94 of the transition portion 80 are configured to afford passage of the second gas supply line 82 and the second gas return line 84, as well as the insulating sheath 162, therethrough.

As depicted in FIGS. 6, 7, and 9, the second portion 92 of the transition portion 80 extends through the third internal cavity 68 of the head portion 20. The second portion 92 is formed from a tubular elbow portion 170, and includes a first end 172 and a second end 174. The second portion 92 is attached at the first end 172 to the first portion 90, and attached at the second end 174 to the third portion 172. Furthermore, the tubular elbow portion 170 includes an internal cavity 176 extending between the first end 172 and the second end 174. The internal cavity 176 communicates with the internal cavities extending through the first portion 90 (including the internal cavity 118, the internal cavity 146, the first internal cavity portion 156, and the second internal cavity portion 158). The internal cavity 176 is sized at least to afford passage of the insulating sheath 162 therethrough.

As depicted in FIGS. 6, 7, and 9, the third portion 94 of the transition portion 80 extends from the inside to the outside of the head portion 20. The third portion 94 is formed from a flange portion 180 and a tubular portion 182 attached to one another, and includes a first end 184 and a second end 186. The third portion 94 is attached at the first end 184 to the second portion 92, and, as discussed below, the tubular portion 182 is threaded to receive a portion of the probe portion 18 thereon. Furthermore, the flange portion 180 and the tubular portion 182 includes an interior cavity 188 extending between the first end 184 and the second end 186. The internal cavity 188 communicates with the internal cavities extending through the first portion 90 (including the internal cavity 118, the internal cavity 146, the first internal cavity portion 156, and the second internal cavity portion 158) and the second portion 92 (including the internal cavity 176). The internal cavity 188 is sized at least to afford passage of the insulating sheath 162 therethrough.

The probe portion 18, as depicted in FIGS. 6, 7, and 9, includes a coupler portion 200 and a probe shaft 202. The coupler portion 200 facilitates attachment of the probe portion 18 to the head portion 20, and the probe shaft 202 is configured for insertion into the body of the patient. The coupler portion 200 is formed from a flange portion 204 and a body portion 206, and includes a first end 208 and a second end 210. The flange portion 204 is configured to be received on the interior of head portion 20 in the fourth cavity 69.

The coupler portion 200 includes a first internal cavity portion 212, a second internal cavity portion 213, a third internal cavity portion 214, a fourth internal cavity portion 215, and a fifth internal cavity portion 216. The first internal cavity portion 212 extends through the flange portion 204 and a portion of the body portion 206, and the second internal cavity portion 213, the third internal cavity portion 214, the fourth internal cavity portion 215, and the fifth internal cavity portion 216 extend through the body portion 206. A first opening 220 communicating with the first internal cavity portion 212 is provided in the flange portion 204 at the first end 208 of the coupler portion 200, and a second opening 222 communicating with the fifth internal cavity portion 216 is provided in the body portion 206 at the second end 210.

The second internal cavity portion 213 is threaded to complement the threads provided on the tubular portion 182 of the third portion 94. As such, the tubular portion 182 can be received in second cavity portion 213, and the threads thereof can be engaged to attach the probe portion 18 to the transition portion 80. When the threads of the tubular portion 182 and the second cavity portion 213 are engaged, the flange portion 180 of the third portion 94 is received in the first internal cavity 212 of the coupler portion 200.

The second internal cavity portion 213 and the third internal cavity portion 214 are sized to receive an internal bushing 224 to support the passage of the insulating sheath 162 (and hence, the second gas return line 84 and the second gas supply line 82) during passage thereof through the coupler portion 200. The internal bushing 224 includes a passage 226 therethrough. The passage 226 can be sized to complement the external dimensions of the insulating sheath 162, and the insulating sheath 162 and internal bushing 224 can be welded or brazed to one another therein to facilitate a connection therebetween. As such, the connection between the insulating sheath 162 can serve in holding the insulating sheath 162 in position as it extends through the coupler portion 200. Furthermore, the internal bushing 224 can be "sandwiched" between the second end 186 of the third portion 94 of the transition portion 80 and an internal shoulder 228 formed in the coupler portion 200.

The fourth internal cavity portion 215 and the fifth internal cavity portion 216 are sized to receive a portion of the probe shaft 202 therein, and the probe shaft 202 extends outwardly from the coupler through the second opening 222. For example, the internal dimensions of the fifth internal cavity portion 216 can be sized to complement the external dimensions of the probe shaft 202. The fit between the probe shaft 202 and the fifth internal cavity portion 216 can be fluid tight. The fluid-tight fitment between the probe shaft 202 and the fifth internal cavity portion 216 can be effectuated by welding or brazing. As such, the fit between the probe shaft 202 and the fifth internal cavity portion 216 can serve in attaching the probe shaft 202 to the coupler portion 200.

Figure 10:
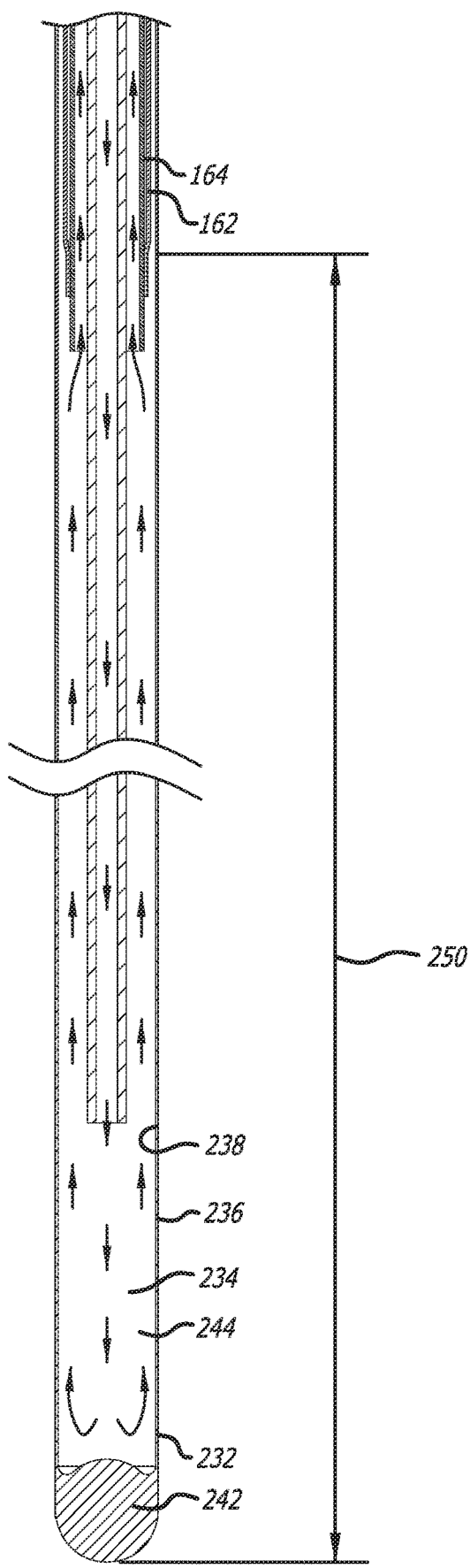
FIG. 10 is an enlarged cross-sectional view of yet another portion of the probe portion of the cryoprobe of FIG. 6.

As depicted in FIGS. 9 and 10, the probe shaft 202 includes a first end 230 and a second end 232, and the second end 232 corresponds to the distal end 14 of the cryoprobe 10. Furthermore, the probe shaft 202 is hollow and includes an internal cavity 234. The probe shaft 202 includes an exterior surface 236 and an interior surface 238 includes an opening 240 at the first end 230, and a tip 242 at the second end 232. The internal cavity 234 and the opening 240 are sized to receive the insulating sheath 162 (and hence, the second gas return line 84 and the second gas supply line 82) therethrough. Furthermore, the insulating sheath 162, the second gas return line 84, and the second gas supply line 82 terminate inside the internal cavity 234. As depicted in FIG. 10, the second gas supply line 82 extends beyond the second gas return line 84, and the second gas return line 84 extends beyond the insulating sheath 162. An expansion area 244 in the internal cavity 234 adjacent the terminal end of the second gas supply line 82 is provided to afford operation of the Joule-Thomson effect. As depicted in FIG. 10, the supply gas exiting the second gas supply line 82 enters the expansion area 244.

The supply gas is supplied to the expansion area 244 from the cryogenic gas supply through the cryoprobe 10 via travel through the first gas supply line 52 and the second gas supply line 82. As discussed above, the first gas supply line 52 and the second gas supply line 82 traverse various components of the cryoprobe 10. To illustrate, the first gas supply line 52 extends from the end portion 16 through the first gas return line 54 and a portion of the transition portion 80. The second gas supply line 82 is connected to the first gas supply line 52 in the transition portion 80. From the connection with the first gas supply line 52, the second gas supply line 82 extends through the transition portion 80 and enters the second gas return line 84 inside the transition portion 80. The second gas return line 84 with the second gas supply line 84 received therein extends through portions of the transition portion 80, and then through portions of the probe portion 18. As discussed above, the second gas supply line 82 and the second gas return line 84 terminate in the probe 202 adjacent the distal end 14.

As discussed above, the supply gas is provided at a high pressure (e.g., ranging from 3000 to 3400 psi). The expansion of the supply gas entering the expansion area 244 immediately decreases in temperature due to the Joule-Thomson effect. As such, the supply gas is further cooled by the Joule-Thomson effect. The cryogenic temperatures of the cooling gas in the expansion area 244 cools an end portion 250 of the probe shaft 202. The end portion 250 of the probe shaft 202 can be made of a material facilitating transfer of the cryogenic temperatures thereto. As discussed above, the cryoprobe 10 can be used to ablate unwanted tissue in the body of the patient. To that end, the end portion 250 can be positioned adjacent the unwanted tissue (such as a cancerous tumor) that is to be ablated. The cryogenic temperatures generated at the end portion 250 facilitates heat transfer from the adjacent tissue, and in doing so, freezes the unwanted tissue. An ice ball of frozen unwanted tissue forms around the end portion 250. Freezing in this manner serves to ablate the unwanted tissue.

As depicted in FIGS. 8-10, after the supply gas is supplied to the expansion area 244, the return gas is returned to adjacent the end portion 16 through the cryoprobe 10 via travel through the second gas return line 84, the transition portion 80, and the first gas return line 54. As discussed above, the second gas supply line 84, the transition portion 80, and the first gas return line 54 traverse various components of the cryoprobe 10. To illustrate, the second gas return line 84 extends through a portion of the probe shaft 202 and the coupler portion 200. From the coupler portion 200, the second gas return line 84 extends through portions of the transition portion 80. The return gas travels through the path of the second gas return line 84 and around the second gas supply line 82 to arrive in the internal cavity 118 of the first sleeve portion 100 of the transition portion 80.

The first sleeve portion 100 includes an aperture 260 formed therein between the interior surface 116 and the exterior surface 114 thereof. As depicted in FIGS. 6-8, the aperture 260 affords passage of the return gas from the internal cavity 118 into the gap 120. Additional apertures (not shown) can be provided in the first sleeve portion 100 to afford passage of the return gas from the internal cavity 118 into the gap 120. For example, additional apertures can be spaced 90°, 180°, and 270° apart from the aperture 260. After exiting the aperture 260, the return gas enters the gap 120 between the first gas return line 54 and the first sleeve portion 100. From the gap 120, the return gas travels through the path of the first gas return line 54 and around the first gas supply line 52 to arrive at the end of the first gas return line 54.

Figure 11:
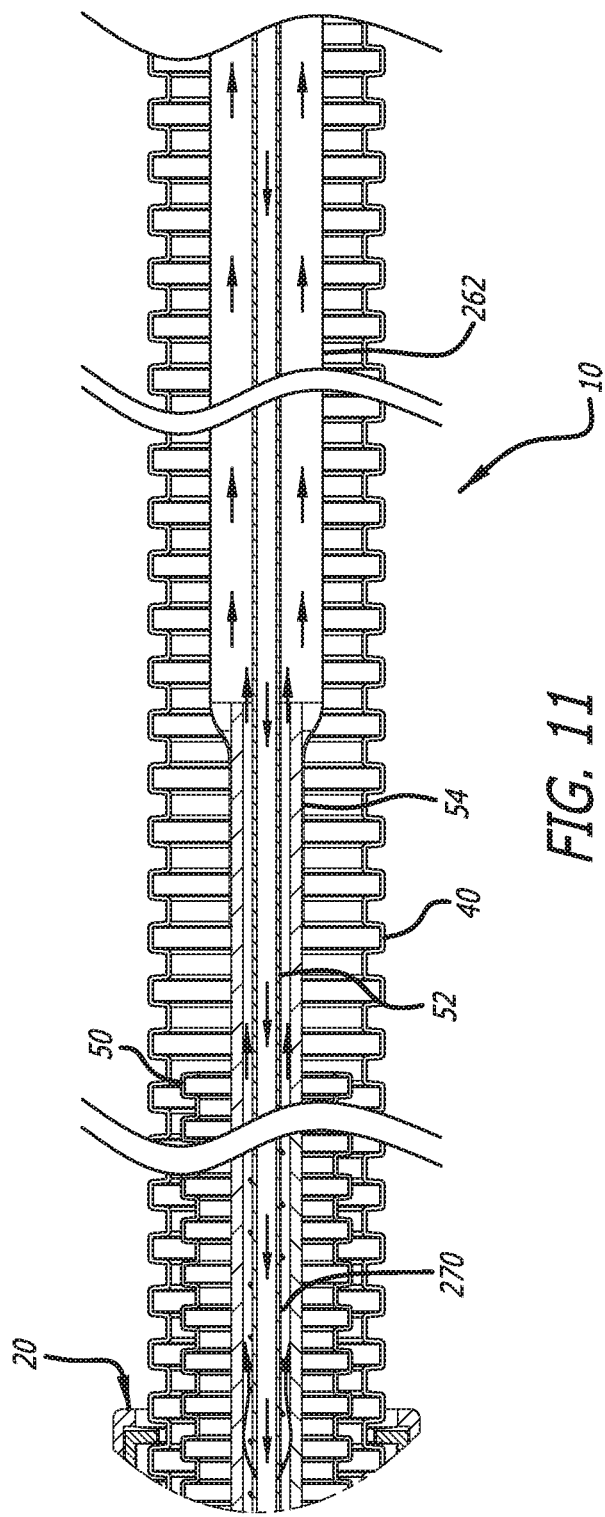
FIG. 11 is an enlarged cross-sectional view of the interior of an exterior tube of the cryoprobe of FIG. 1.

As depicted in FIG. 11, the end of the first gas return line 54 is attached to an expansion tube 262. The expansion tube 262 extends between the end of the first gas return line 54 and the end portion 16. The expansion tube 262 serves as a muffler to decrease the noise of the return gas traveling through the cryoprobe 10. The expansion tube 262 communicates with an exit aperture 264 formed in the end portion 16, and the return gas can be expelled from the cryoprobe 10 through the exit aperture 264. Like the exterior tube 40, the interior tube 50, the first gas return line 54, and the first gas supply line 52, the expansion tube 262 can be flexible. The flexibility of the exterior tube 40, the interior tube 50, the first gas return line 54, the first gas supply line 52, and the expansion tube 262 affords manipulation thereof during surgery to afford positioning and repositioning of the head portion 20.

Flow of the return gas during travel thereof through the cryoprobe 10 can be used to precool the supply gas. As discussed above, the return gas travels around the second gas supply line 82 as it travels through the second gas return line 84, and travels around the first gas supply line 52 as it travels through the first gas return line 54. During such travel around the second gas supply line 82 and the first gas supply line 52, the return gas can be used to precool the supply gas traveling through the second gas supply line 82 and the first gas supply line 52, respectively. To increase the heat exchanging effects of the colder return gas on the supply gas, the first gas supply line 52, the second gas supply line 82, and the second gas return line 84 can be made of metallic materials to facilitate heat transfer between the supply gas and the return gas. Furthermore, to additionally increase the heat exchanging effects of the colder return gas on the supply gas, the spaces between the second gas supply line 82 and the second gas return line 84 and between the first gas supply line 52 and the first gas return line 54 can include turbulence inducing structures to increase turbulence in the flow of the return gas. Increased turbulence in the flow of the return gas insures contact of the return gas with the second gas supply line 82 and the first gas supply line 52, and such contact of the colder return gas serves to remove heat from the supply gas flowing through the second gas supply line 82 and the first gas supply line 52. For example, the space between the first gas supply line 52 and the first gas return line 54 can be provided with a turbulence inducer 270. A similar turbulence inducer can also be provided in the space between the second gas supply line 82 and the second gas return line 84. The turbulence inducer 270 has a helical structure wrapped around the first gas supply line 52 that induces eddy currents in the return gas to increase contact of the return gas with the first gas supply line 52. The turbulence inducer 270 can also be formed as baffles and/or protrusions such as bumps, fins, and/or ribs formed on the exterior surface of the first gas supply line 52.

In addition to the insulating sheath 162 (and the insulative cavity 164 formed in part thereby), the gaps between exterior tube 40, the interior tube 50, the first gas return line 54, and the expansion tube 262 serve in insulating these portions of the cryoprobe 10 from the warming by the outside environment and against the cooling effect of the cooling gas traveling through the cryoprobe 10. Additionally, the gaps between the insulating sheath 162 and the interior surfaces of the second internal cavity portion 158 (of the first portion 90), the internal cavity 176 (of the second portion 92), and the internal cavity 188 (of the third portion 94) serve in insulating these portions of the cryoprobe 10 from the warming by the outside environment and against the cooling effect of the cooling gas traveling through the cryoprobe 10. Similarly, the first internal cavity 64, the second internal cavity 66, the third internal cavity 68, and other internal cavities in the head portion 20 serve to insulate the cryoprobe 10 from the heat from a user's hand and from the cooling effect of the cooling gas traveling through the cryoprobe 10.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A cryoprobe for use during surgery in a human body to remove unwanted tissue, the cryoprobe comprising:
   a proximal end and a distal end opposite from one another;
   a first gas supply line and a second gas supply line for delivering a supply of cryogenic gas from at least adjacent the proximal end to at least adjacent the distal end, the first gas supply line being connected to a supply of cryogenic gas;
   a first gas return line and a second gas return line for returning the supply of cryogenic gas from at least adjacent the distal end to at least adjacent the proximal end;
   a first portion of the first gas supply line extending through a first portion of the first gas return line;
   at least one turbulence inducer provided in the first gas return line between the first gas supply line and the first gas return line;
   a transition portion having a proximal first end, a distal second end, at least one internal cavity extending between the proximal first end and the distal second end, and an aperture positioned between the proximal first end and the distal second end and extending from the internal cavity to an exterior portion of the transition portion, an end of a second portion of the first gas return line being attached to the transition portion, an end of a second portion of the first gas supply line being received in the internal cavity of the transition portion, an end of a first portion of the second gas supply line being received in the internal cavity of the transition portion, and an end of a first portion of the second gas return line being received in the transition portion, the end of the second portion of the first gas supply line and the end of the first portion of the second gas supply line being attached to one another at a coupling therebetween located within the internal cavity of the transition portion, the coupling being closer to the proximal end than an attachment location of the end of the second portion of the first gas return line and the transition portion, and a portion of the second portion of the first gas return line surrounding the transition portion to form a gap therebetween along a first length of the transition portion adjacent the proximal first end, the internal cavity communicating with the gap via the aperture in the transition portion; and
   a probe portion including a shaft portion, the shaft portion including a first end, a second end, and an interior cavity extending from adjacent the first end to adjacent the second end, the shaft portion including an opening into the interior cavity at the first end, and a tip at the second end, a second portion of the second gas return line extending into the interior cavity of the shaft portion, a second portion of the second gas supply line extending through the second portion of the second gas return line, the second portion of the second gas return line terminating at an end within the interior cavity and the second portion of the second gas supply line terminating at an end within the interior cavity, the end of the second portion of the second gas supply line being closer to the tip than the end of the second portion of the second gas return line;
   wherein portions of the second portion of the first gas supply line, the first portion of the second gas supply line, and the second portion of the first gas return line are concentric with one another adjacent the aperture, and
   wherein the cryogenic gas is supplied to the interior cavity of the shaft portion via travel through at least the first gas supply line and the second gas supply line, and the cryogenic gas is returned to at least adjacent the proximal end via travel through at least the second gas return line, the transition portion, and the first gas return line, the cryogenic gas being returned first flowing around the second gas supply line in the second gas return line, the cryogenic gas being returned second flowing into the internal cavity of the transition portion from the second gas return line, the cryogenic gas being returned third flowing through the aperture in the transition portion from the internal cavity of the transition portion to the gap between the second portion of the first gas return line and the transition portion, the cryogenic gas being returned fourth flowing around the second gas supply line in the first gas return line from the gap between the first gas return line and the transition portion, the at least one turbulence inducer creating turbulence in the cryogenic gas being returned flowing through the first gas return line.

2. The cryoprobe of claim 1, wherein the cryogenic gas is one of Argon, Krypton, Xenon, CO2, N2O, and N2.

3. The cryoprobe of claim 1, wherein the at least one turbulence inducer is a helical structure extending from adjacent the transition portion toward the proximal end of the cryoprobe.

4. The cryoprobe of claim 1, wherein the at least one turbulence inducer is a plurality of fins provided on the first gas supply line.

5. The cryoprobe of claim 1, further comprising a body portion including an exterior tube, the exterior tube having a first end and a second end spaced apart from one another, the first end of the exterior tube being provided adjacent the proximal end of the cryoprobe, the first portion of the first gas return line extending through at least a portion of the exterior tube.

6. The cryoprobe of claim 1, further comprising a head portion including at least one interior cavity extending therethrough, the transition portion being at least partially received in the head portion, the second portion of the first gas return line and the second portion of the first gas supply line extending into the head portion.

7. The cryoprobe of claim 6, further comprising the probe portion including a coupler portion, the coupler portion being attached to the head portion, and the shaft portion extending outwardly from the coupler portion.

8. The cryoprobe of claim 1, wherein the cryogenic gas returned through at least the first gas return line, the transition portion, and the second gas return lines is expelled from the cryoprobe through at least one aperture provided adjacent the proximal end.

9. A cryoprobe for use during surgery in a human body to remove unwanted tissue, the cryoprobe comprising:
   a proximal end and a distal end opposite from one another;
   a first gas supply line and a second gas supply line for delivering a supply of cryogenic gas from at least adjacent the proximal end to at least adjacent the distal end, the first gas supply line being connected to a supply of cryogenic gas;

a first gas return line and a second gas return line for returning the supply of cryogenic gas from at least adjacent the distal end to at least adjacent the proximal end;

a first portion of the first gas supply line extending through a first portion of the first gas return line;

a head portion including at least one interior cavity extending therethrough, the head portion including a transition portion being at least partially received in the at least one interior cavity, the transition portion having a proximal first end, a distal second end, at least one internal cavity extending between the proximal first end and the distal second end, and an aperture_ positioned between the proximal first end and the distal second end and extending from the internal cavity to an exterior portion of the transition portion, a second portion of the first gas return line and a second portion of the first gas supply line extending into the head portion, an end of the second portion of the first gas return line being attached to the transition portion-, an end of the second portion of the first gas supply line being received in the internal cavity of the transition portion, an end of a first portion of the second gas supply line being received in the internal cavity of the transition portion, and an end of a first portion of the second gas return line being received in the transition portion, the end of the second portion of the first gas supply line and the end of the first portion of the second gas supply line being attached to one another at a coupling therebetween located within the internal cavity of the transition portion, the coupling being closer to the proximal end than an attachment location of the end of the second portion of the first gas return line and the transition portion, and a portion of the second portion of the first gas return line surrounding the transition portion to form a gap therebetween along a first length of the transition position adjacent the proximal first end, the internal cavity communicating with the gap via the aperture in the transition portion; and a probe portion attached to the head portion, the probe portion including a coupler portion and a shaft portion, the coupler portion being attached to the head portion, and the shaft portion extending outwardly from the coupler portion, the shaft portion including a first end, a second end, and an interior cavity extending from adjacent the first end to adjacent the second end, the shaft portion including an opening into the interior cavity at the first end, and a tip at the second end, a second portion of the second gas return line extending from the head portion through the coupler portion and into the interior cavity of the shaft portion, and a second portion of the second gas supply line extending through the second portion of the second gas return line, the second portion of the second gas return line terminating at an end within the interior cavity and the second portion of the second gas supply line terminating at an end within the interior cavity, the end of the second portion of the second gas supply line being closer to the tip than the end of the second portion of the second gas return line;

wherein portions of the second portion of the first gas supply line, the first portion of the second gas supply line, and the second portion of the first gas return line are concentric with one another adjacent the aperture, and wherein the cryogenic gas is supplied to the interior cavity of the shaft portion via travel through at least the first gas supply line and the second gas supply line, and the cryogenic gas is returned to at least adjacent the proximal end via travel through at least the second gas return line, the transition portion, and the first gas return line, the cryogenic gas being returned first flowing around the second gas supply line in the second gas return line, the cryogenic gas being returned second flowing into the internal cavity of the transition portion from the second gas return line, the cryogenic gas being returned third flowing through the aperture in the transition portion from the internal cavity of the transition portion to the gap between the second portion of the first gas return line and the transition portion, the cryogenic gas being returned fourth flowing around the first gas supply line in the first gas return line from the gap between the first gas return line and the transition portion.

10. The cryoprobe of claim 9, further comprising at least one turbulence inducer provided in the first gas return line between the first gas supply line and the first gas return line, the at least one turbulence inducer creating turbulence in the cryogenic gas being returned flowing through the first gas return line.

11. The cryoprobe of claim 10, wherein the at least one turbulence inducer is a helical structure extending from the adjacent the transition portion toward the proximal end of the cryoprobe.

12. The cryoprobe of claim 10, wherein the at least one turbulence inducer is a plurality of fins provided on the first gas supply line.

13. The cryoprobe of claim 9, further comprising a body portion including an exterior tube, the exterior tube having a first end and a second end spaced apart from one another, the first end of the exterior tube being provided adjacent the proximal end of the cryoprobe, the first portion of the first gas return line extending through at least a portion of the exterior tube.

14. The cryoprobe of claim 9, wherein the cryogenic gas returned through at least the first gas return line, the transition portion, and the second gas return lines is expelled from the cryoprobe through at least one aperture provided adjacent the proximal end.

15. A cryoprobe for use during surgery in a human body to remove unwanted tissue, the cryoprobe comprising:

a proximal end and a distal end opposite from one another;

a first gas supply line and a second gas supply line for delivering a supply of cryogenic gas from at least adjacent the proximal end to at least adjacent the distal end, the first gas supply line being connected to a supply of cryogenic gas;

a first gas return line and a second gas return line for returning the supply of cryogenic gas from at least adjacent the distal end to at least adjacent the proximal end;

a first portion of the first gas supply line extending through a first portion of the first gas return line;

a head portion including at least one interior cavity extending therethrough, the head portion including a transition portion being at least partially received in the at least one interior cavity, the transition portion having a proximal first end, a distal second end, at least one internal cavity extending between the proximal first end and the distal second end, and an aperture_ positioned between the proximal first end and the distal second end and extending from the internal cavity to an exterior portion of the transition portion, a second portion of the first gas return line and a second portion of the first gas supply line extending into the head portion, an end of the second portion of the first gas return line being attached to the transition portion-, an end of the second portion of the first gas supply line being received in the internal cavity of the transition portion, an end of a first portion of the second gas supply line being connected to the internal cavity of the transition portion, and an end of a first portion of the second gas return line being received in the transition portion, the end of the second portion of the first gas supply line and the end of the first portion of the second gas supply line being attached to one another at a coupling therebetween located within the internal cavity of the transition portion, the coupling being closer to the proximal end than an attachment location of the end of the second portion of the first gas return line and the transition portion, and a portion of the second portion of the first gas return line surrounding the transition portion to form a gap therebetween along a first length of the transition position adjacent the proximal first end, the internal cavity communication with the gap via the aperture in the transition portion; and a probe portion attached to the head portion, the probe portion including a coupler portion and a shaft portion, the coupler portion being attached to the head portion, and the shaft portion extending outwardly from the coupler portion, the shaft portion including a first end, a second end, and an interior cavity extending from adjacent the first end to adjacent the second end, the shaft portion including an opening into the interior cavity at the first end, and a tip at the second end, a second portion of the second gas return line extending from the head portion through the coupler portion and into the interior cavity of the shaft portion, and a second portion of the second gas supply line extending through the second portion of the second gas return line, the second portion of the second gas return line terminating at an end within the interior cavity and the second portion of the second gas supply line terminating at an end within the interior cavity, the end of the second portion of the second gas supply line being closer to the tip than the end of the second portion of the second gas return line;

wherein portions of the second portion of the first gas supply line, the first portion of the second gas supply line, and the second portion of the first gas return line are concentric with one another adjacent the aperture, and wherein the cryogenic gas is supplied to the interior cavity of the shaft portion via travel through at least the first gas supply line and the second gas supply line, and the cryogenic gas is returned to at least adjacent the proximal end via travel through at least the second gas return line, the transition portion, and the first gas return line, the cryogenic gas being returned first flowing around the second gas supply line in the second gas return line, the cryogenic gas being returned second flowing into the internal cavity of the transition portion from the second gas return line, the cryogenic gas being returned third flowing through the aperture in the transition portion from the internal cavity of the transition portion to the gap between the second portion of the first gas return line and the transition portion, the cryogenic gas being returned fourth flowing around the first gas supply line in the first gas return line from the gap between the first gas return line and the transition portion.

16. The cryoprobe of claim 15, further comprising at least one turbulence inducer provided in the first gas return line between the first gas supply line and the first gas return line, the at least one turbulence inducer creating turbulence in the cryogenic gas being returned flowing through the first gas return line.

17. The cryoprobe of claim 16, wherein the at least one turbulence inducer is a helical structure extending from the adjacent the transition portion toward the proximal end of the cryoprobe.

18. The cryoprobe of claim 16, wherein the at least one turbulence inducer is a plurality of fins provided on the first gas supply line.

19. The cryoprobe of claim 15, wherein at and adjacent the coupling between the end of the second portion of the first gas supply line and the end of the first portion of the second gas supply line, the second portion of the first gas supply line, the first portion of the second gas supply line, and the second portion of the first gas return line being coaxial with one another.

20. The cryoprobe of claim 1, wherein at and adjacent the coupling between the end of the second portion of the first gas supply line and the end of the first portion of the second gas supply line, the second portion of the first gas supply line, the first portion of the second gas supply line, and the second portion of the first gas return line being coaxial with one another.

21. The cryoprobe of claim 9, wherein at and adjacent the coupling between the end of the second portion of the first gas supply line and the end of the first portion of the second gas supply line, the second portion of the first gas supply line, the first portion of the second gas supply line, and the second portion of the first gas return line being coaxial with one another.

22. The cryoprobe of claim 9, wherein the cryogenic gas is one of Argon, Krypton, Xenon, CO2, N2O, and N2.

23. The cryoprobe of claim 15, wherein the cryogenic gas is one of Argon, Krypton, Xenon, CO2, N2O, and N2.

* * * * *